United States Patent [19]
Morse

[11] Patent Number: 5,650,856
[45] Date of Patent: Jul. 22, 1997

[54] FIBER LASER INTRA-CAVITY SPECTROSCOPE

[75] Inventor: Theodore F. Morse, Little Compton, R.I.

[73] Assignee: Brown University Research Foundation, Providence, R.I.

[21] Appl. No.: 491,269

[22] Filed: Jun. 16, 1995

[51] Int. Cl.$^6$ .......................... G01N 21/31; G01N 21/35; G01N 21/39
[52] U.S. Cl. .................. 356/436; 356/437; 372/7
[58] Field of Search ..................... 356/440, 436, 356/437; 372/6; 385/12

[56] References Cited

U.S. PATENT DOCUMENTS

| | | | |
|---|---|---|---|
| 5,245,405 | 9/1993 | Mitchell et al. | 356/301 |
| 5,268,736 | 12/1993 | Prather | 356/440 |
| 5,337,401 | 8/1994 | Onishi et al. | 372/6 X |
| 5,493,113 | 2/1996 | Dunphy et al. | 356/345 X |

FOREIGN PATENT DOCUMENTS

| | | | |
|---|---|---|---|
| 435217 | 7/1991 | European Pat. Off. | 372/6 |
| 56-107149 | 8/1981 | Japan | 356/440 |

OTHER PUBLICATIONS

Atkins, R.M. et al. (1993) "Mechanisms of enhanced UV photosensitivity via hydrogen loading in germanosilicate glasses" *Electronics Letters* 29(14):1234–1235.

Atmanspacher, H. et al. (1985) "Dynamics of laser intracavity absorption" *The American Physical Society* 32(1):254–268.

Ball, G.A. et al. (1993) "Low Noise Single Frequency Linear Fibre Laser" *Electronics Letters* 29(18):1623–1625.

Böhm R. et al. (1993) "Intracavity absorption spectroscopy with a Nd3+ –doped fiber laser" *Optics Letters* 18(22):1955–1957.

Burakov, V.S. "Development of Intercavitary Laser Spectroscopy" Plenum Publishing Corporation pp. 843–854.

Gupta, B.D. and C.D. Singh (1994) "Fiber–Optic Evanescent Field Absorption Sensor: A Theoretical Evaluation" *Fiber and Integrated Optics* 13(4):433–443.

Hale, Z.M. and F.P. Payne (1994) "Demonstration of an optimised evanescent field optical fibre sensor" *Analytica Chimica Acta* 293:49–54.

Hänsch, T.W. et al. (1985) "Ultrasensitive Response of a CW Dye Laser to Selective Extinction" *IEEE Journal of Quantum Electronics* QE-8(10):802–803.

Henry W. (1994) "Evanescent field devices: a comparison between tapered optical fibres and polished or D–fibres" *Optical and Quantum Electronics* 26(3):s261–s272.

(List continued on next page.)

Primary Examiner—Vincent P. McGraw
Attorney, Agent, or Firm—Thomas J. Engellenner; Anthony A. Laurentano; Lahive & Cockfield

[57] ABSTRACT

The present invention is directed to methods and apparatus for detecting species in a laser cavity. According to one preferred embodiment, a device according to the invention includes: a source of excitation energy at a first wavelength; a first optic fiber; a resonant cavity; an absorption element; and a detector element. The first optic fiber has at least a first portion which is lasant-doped, and is optically coupled to the excitation source. The doping causes the first optic fiber to amplify light. Thus, in response to light coupled from the excitation source, the first optic fiber is capable of lasing. The resonant cavity surrounds the first portion of the optic fiber and has at least a first wavelength-specific reflector, such that laser light at only a second wavelength is amplified in the cavity. The absorption element can expose a sample to the light contained within the resonant cavity. The detector is optically coupled to the resonant cavity. It detects variations in the intensity of the laser light within the resonant cavity. By detecting variations in the intensity of the light in the cavity, the detector can indicate the presence of particular species.

43 Claims, 2 Drawing Sheets

OTHER PUBLICATIONS

Hill, K.O. et al. (1993) "Bragg gratings fabricated in momo-mode photosensitive optical fiber by UV exposure through a phase mask" *Appl. Phys. Lett.* 62(10):1035–37.

Hill K.O. et al. (1993) "Photosensitivity in optical fibers" *Annu. rev. Mater. Sci.* 23;125–127.

Meltz, G. (1989) "Formation of Bragg gratings in optical fibers by a transverse holographic method" *Optical Society of America* 14(15):823–825.

Messica, A. et al. (1994) "Fiber–optic evanescent wave sensor for gas detection" *Optics Letters* 19(15):1167–1169.

Morey, W.W. et al. (1994) "Photoinduced Bragg Gratings in Optical Fibers" *Optics & Photonics News* Feb.:8–14.

Prohaska, J.D. et al. (1994) "Theoretical description of fiber Bragg reflectors prepared by Fresnel diffraction images" *Applied Optics* 33(18):3896–3900.

FIBER LASER INTRA-CAVITY SPECTROSCOPE

This invention was made with government support under the following Contract Numbers. Grant No. ECS-9500584 awarded by the National Science Foundation; Grant No. F30602-95-C-0092 awarded by the Air Force; and Grant No. DAAH04-95-1-0025 awarded by the Army. The government has certain rights in this invention.

BACKGROUND

The present invention generally relates to intra-cavity spectroscopy. More specifically, the invention is directed to methods and apparatus for identifying a compound which is exposed to a light wave resonating within a laser cavity.

Absorption cell spectroscopy has been used for many years. According to some conventional methods, white light is coupled through an absorption cell and subsequently scanned by a monochrometer. When absorption occurs in the cell at a particular wavelength, as measured by the output of the monochrometer, there is a decrease in the intensity of the light in accordance with Beer's law given by:

$$I(L,\lambda)=I_0(0,\lambda)e^{-\alpha_\lambda L}$$

where L is the length of the absorption cell. The intensity of the light entering the absorption cell as a function of wavelength is $I_0(0,\lambda)$ and the light exiting the absorption cell is $I(L,\lambda)$. The absorption coefficient $\alpha_\lambda$ depends upon the wavelength, the number of absorbers and the molecular cross section of the absorption species.

According to other conventional methods, instead of a white light source, a tunable laser source is employed to couple laser light through the absorption chamber. When the laser wavelength coincides with an absorption wavelength of the species in the absorption chamber, the intensity of the light passing through the absorption chamber decreases in accord with Beer's law.

Since the sensitivity of the detection of the species present in the absorption cell is exponentially dependent upon the length of the absorption cell, this sensitivity can be increased by increasing the path length of light though the absorption cell. To this end, some prior approaches attempt to increase the sensitivity by passing the light through the absorption cell a plurality of times.

According to other conventional methods, the absorption cell is located inside the laser cavity. If a species which absorbs light at the lasing frequency is placed in the laser cavity, the output intensity of the laser drops. Photons make many round trips before exiting the cavity. The effective absorption interaction path length is significantly increased by this technique. This approach is generally known to increase the sensitivity of measurements by several orders of magnitude.

Several prior art approaches have been employed to create laser cavities which incorporate absorption cells. By way of example, fiber optic lasers have recently been employed. According to one conventional method, a neodymium doped fiber of approximately two meters in length is pumped by an argon ion laser or by a diode laser. An open portion of the laser cavity, which is approximately 35 cm long, is defined between two dielectric mirrors and is filled with a sample having an unknown quantity of an absorbing species (water vapor). The output intensity of the laser is monitored by a spectrometer. The monitored intensity decreases as the quantity of absorption species present in the sample increases.

Although laser spectroscopy has improved over the past few years, several disadvantages persist in conventional intra-cavity systems. By way of example, conventional systems tend to require expensive components and do not lend themselves to mass production. Conventional systems also tend to be too large to easily transport to field locations. Additionally, such systems typically require considerable adjustment to align the required optical components. Further, conventional systems typically may not provide a convenient method for tuning the laser cavity to examine the absorption characteristics of the absorber species over a plurality of frequencies.

Accordingly, an object of the present invention is to provide an inexpensive device for fiber laser intra-cavity spectroscopy.

Another object of the invention is to provide a compact device for fiber laser intra-cavity spectroscopy which is more convenient for field applications.

A further object of the invention is to provide a conveniently tunable fiber laser intra-cavity spectroscope.

SUMMARY OF THE INVENTION

The invention relates to methods and apparatus for detecting species in a laser cavity. According to one preferred embodiment, the invention is directed to a spectroscopic analyzing apparatus. The apparatus includes: a source of excitation energy at a first wavelength; a first optic fiber; a resonant cavity; an absorption element; and a detector element. The first optic fiber has at least a first portion which is lasant-doped, and is optically coupled to the excitation source. The doping causes the first optic fiber to amplify light. Thus, in response to light coupled from the excitation source, the first optic fiber is capable of lasing. The resonant cavity surrounds (e.g. is continuous with) the first portion of the optic fiber and has at least a first wavelength-specific reflector, such that laser light at only a second wavelength is amplified in the cavity. The absorption element can expose a sample to the light contained within the resonant cavity. By way of example, the absorption element can be a chamber where a sample can be placed. The detector is optically coupled to the resonant cavity. It detects variations in the intensity of the laser light within the resonant cavity. If a species which absorbs light at the lasing wavelength is placed within the absorption chamber, the intensity of the laser light in the chamber diminishes. Thus, by detecting variations in the intensity of the light in the cavity, the detector can indicate the presence of particular species.

According to a further embodiment of the invention, the first wavelength-specific reflector includes a first Bragg grating imposed on the first optic fiber. The first Bragg grating forms a periodic variation in refractive index of the first optic fiber. The periodic variation can be formed so that the first Bragg grating forms a narrow band mirror which reflects light around the lasing wavelength. In a further embodiment, the apparatus can include an element for compressing the first Bragg grating. By compressing the first Bragg grating, the wavelength at which the grating reflects can be altered. According to the invention, the first Bragg grating can be placed in a deformable ferrule. The ferrule can be compressed by conventional mechanical mechanisms in a selective manner. In this way, the laser cavity can be continuously tuned to lase at a plurality of wavelengths. By sweeping the cavity with a plurality of wavelengths, a plurality of absorption peaks of the species to be detected can be examined.

In one preferred construction of the apparatus, the first wavelength-specific reflector, which is preferably a Bragg grating, reflects most of the light at the lasing wavelength within the laser cavity. However, the grating couples a small portion of that light out of the cavity to the detector element. In this way, the detector element can monitor changes in the intensity of the light in the resonant cavity.

As mentioned above, a first portion of the first optic fiber is rare earth doped. According to one embodiment, the fiber is doped with at least one of lanthanum, cerium, praseodymium, neodymium, promethium, samarium, europium, gadolinium, terbium, dysprosium, holmium, erbium, thulium and ytterbium. According to a further embodiment, the fiber is doped with at least one of holmium and thulium. The concentration with which the fiber is doped is dependent, in part, on the length of the portion which is to be doped. According to one embodiment, the fiber has a length in the approximate range of 3 cm–20 cm, while the doping concentration varies from approximately 300 ppm–3000 ppm.

According to a preferred embodiment of the invention, the lasing wavelength is chosen based primarily on the species to be detected. In general, for a thulium or thulium-holmium doped fiber, lasing wavelengths in the approximate range of 1.65 microns–2.1 microns can be achieved. An 800 nm laser source can be used to pump such a system. This is an advantage, since inexpensive laser diodes can be employed to perform the pumping. As mentioned above, the first Bragg grating can be compressed to tune the lasing wavelength. According to a preferred embodiment, the first Bragg grating can be compressed to providing at least 40 nm of tuning.

In a further embodiment of the invention, the light emitted from the doped portion of the first optic fiber has an initial beam width. This beam width is typically in the approximate range of 5 microns–20 microns, depending on the size of the optical fiber. It is desirable to illuminate as much of the sample as practicable. Consequently, the apparatus can include an optical element for expanding the initial beam diameter, prior to exposing the sample to the laser light. The optical element can be for example, a gradient index lens, an aspheric lens or a lens assembly of the type conventionally designed for such purposes. According to one embodiment, the beam diameter is expanded to be in the approximate range of 1 mm–5 mm.

There are several methods by which the pumping energy can be coupled to the resonant cavity and a portion of the laser light from the resonant cavity can, in turn, be coupled to the detector. By way of example, the apparatus can include a dichroic beam splitter. The beam splitter can couple light at the pumping wavelength from an energy source to the resonant cavity, by way of the first wavelength-specific reflector. The beam splitter can also couple light at the lasing frequency from the laser cavity to the detector by way of the first wavelength selective reflector. The apparatus can also include an optical filter element, coupled between the detector and the pumping source, for ensuring that light at the pumping wavelength is not coupled into the detector.

In a further embodiment of the invention, the resonant cavity has first and second axial ends. The first wavelength-specific reflector is located at the first axial end. The resonant cavity further includes a second wavelength-specific reflector, located at the second axial end of the cavity. The second wavelength-specific reflector reflects light within a predetermined line width of the second wavelength, i.e. the lasing wavelength. In a preferred embodiment, the second wavelength-specific reflector has a line width at least as large as the wavelength range for which the first Bragg grating is capable of sweeping the cavity. According to a further embodiment the second wavelength-specific reflector includes a second Bragg grating formed on second optic fiber which is optically coupled to the second axial end of the resonant cavity. In yet a further embodiment, the second Bragg grating is partially transmissive and couples a portion of the laser light at the lasing wavelength to the detector element. Such a construction has the advantage that it alleviates the need for the dichroic beam splitter.

According to yet another embodiment of the invention, the laser light amplified in the resonant cavity couples along the first optical fiber between the first Bragg grating and the second Bragg grating. According to this embodiment, the cladding on the a portion of the first optic fiber can be stripped away to expose the evanescent wave to the sample. Since the evanescent wave travels on the outside of the optic fiber, a species which absorbs light at the lasing frequency tends to reduce the intensity of the evanescent wave. Any changes in the evanescent wave effect changes in the intensity of the light wave traveling in the core of the first optic fiber. The second Bragg grating couples a portion of the light traveling in the core of the first optic fiber to the detector element. The detector senses changes in the intensity of the light in the core. Such changes can be correlated to the presence of a species in the sample. The changes in intensity can be further correlated, by way of conventional methods, to determine the concentration of the species in the sample.

BRIEF DESCRIPTION OF THE DRAWINGS

For a fuller understanding of the nature and objects of the present invention, reference should be made to the following detailed description and the accompanying drawings, in which.

DETAILED DESCRIPTION

The invention generally relates to fiber laser spectroscopy. More particularly, the invention is directed to methods and apparatus for detecting a species in a laser cavity formed in part by a wavelength selective reflector, wherein the gain medium of the laser is an optical fiber.

Figure 1:
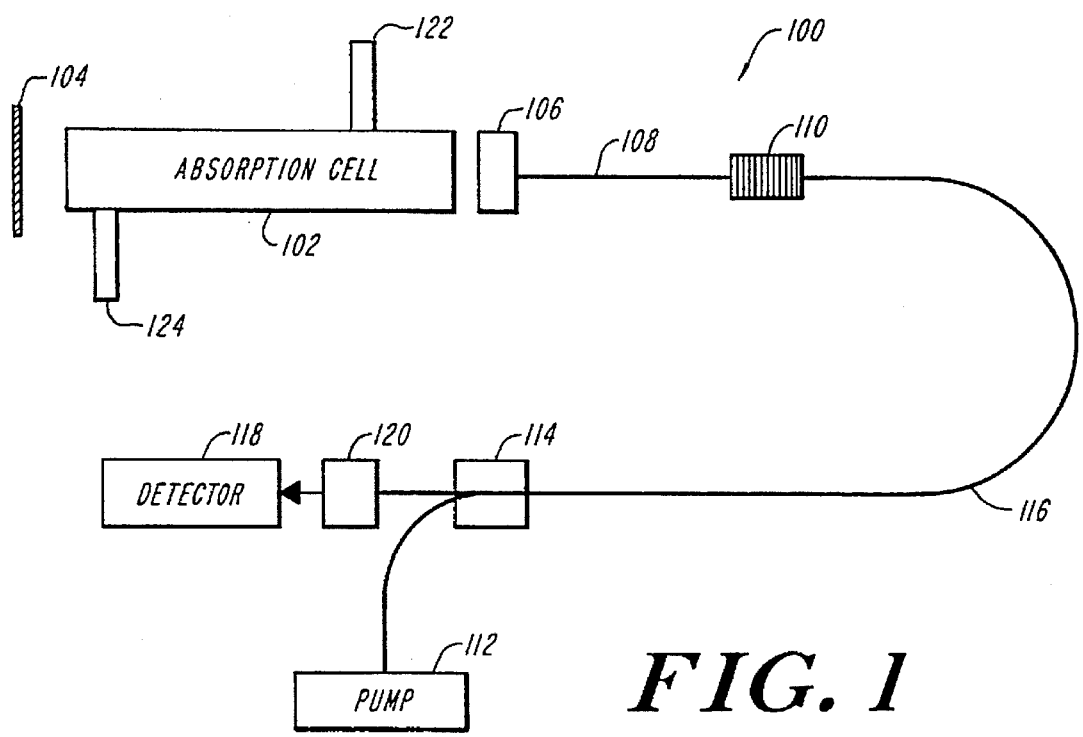
FIG. 1 is a schematic block diagram of a device for fiber laser intra-cavity spectroscopy according to one embodiment of the invention.

FIG. 1 is a schematic block diagram of a fiber laser intra-cavity spectroscope 100 according to one preferred embodiment of the invention. The spectroscope 100 includes a resonant cavity formed from a broad band reflector 104, an optical element 106, a lasant-doped fiber 108 and a wavelength-specific reflector 110. The spectroscope 100 further includes an energy source 112, a wavelength selective coupler 114, an undoped fiber 116, a detector 118 and an optical filter 120. An absorption cell 102 is located within the resonant cavity.

The pump source 112 couples laser light at a first wavelength through the wavelength selective coupler 114. The coupler 114 passes light the light along the undoped optical fiber 116 to the wavelength-specific reflector 110. The wavelength-specific reflector 110 couples the light from the pump source 112 to the doped fiber 108. Any conventional optical fibers can be employed for both fibers 108 and 116. By way of example, according to one embodiment fused silica fibers are used, while in other embodiments, fluoride fibers can be used. In response to the light from the pump source 112, the doped fiber 108 emits light at a second wavelength and couples it to through the absorption cell 102 to the reflector 104. The light from the doped fiber 108 reflects between the broad band reflector 104 and the wavelength specific reflector 110 and continues to be amplified by the doped fiber 108 until light in the cavity resonates at the second wavelength, i.e. the lasing wavelength. The doped fiber 108 can be fusion spliced onto the optical fiber 116, to create a single fiber and to minimize splice losses. Additionally, a narrow line width laser cavity can be maintained, without the use of an isolator because the fiber 116, which is outside of the resonant cavity, contains no laser doping. Without a dopant, no spontaneous emission at the laser wavelength can occur.

The absorption cell 102 can expose a sample (solid, liquid or gas) to the light contained within the resonant cavity. Samples can enter the cell 102 by way of inlet 122. The sample can subsequently be purged from the cell 102 by way of outlet 124. If the sample contains a species which absorbs light at the lasing wavelength, it will cause the intensity of the laser light in the resonant cavity to diminish. The wavelength-specific reflector 110 couples a small portion, preferably less than 10%, of the laser light from the resonant cavity to the coupler 114. The coupler 114 couples light at the lasing wavelength to the detector 118. The detector 118 can sense changes in the intensity of the laser light in the resonant cavity. These changes can be correlated, using conventional processing methods, to differing concentrations of a particular species in the absorption cell 102.

According to a preferred embodiment of the invention, the wavelength-specific reflector 110 is formed from a Bragg grating imposed on either optical fiber 108 or optical fiber 116. The Bragg grating 110 is a periodic variation in the index of refraction imposed on the core of optical fiber 108 or the optical fiber 116. Intense ultraviolet light can produce changes in the index of refraction of an optical fiber, usually doped with germanium. When this is done in a periodic manner, a periodic structure results in the optical fiber. The periodic variation can be formed so that the Bragg grating 110 forms a narrow band reflector, which reflects light around the lasing wavelength. The Bragg grating 110 forms a boundary of the resonant cavity which can be continuous with the optical fiber 108.

The Bragg grating 110 can be constructed by any conventional method, such as phase masking, holography or employment of a prism. In phase masking, an ultraviolet light is directed onto a phase mask. The phase mask generates a 180 degree phase shift between light beams. The out of phase light beams interfere constructively and the zeroth order diffraction (the light that passes normal to the phase mask) is cancelled. The ±1 order diffracted beams form the interference pattern that creates the Bragg grating in the optical fiber. According to the holographic method, two ultraviolet beams interfere in the core of an optical fiber to form the periodic grating. When a prism is employed, reflection within the prism provides different interfering path lengths that can create the alternating optical density pattern on the fiber.

In a further embodiment of the invention, the Bragg grating 110 can be tuned. By tuning the grating 110, the periodic variation in the optical fiber core can be altered, thereby altering the wavelength at which the grating reflects. In this way the resonant cavity can be tuned to change the lasing wavelength. By sweeping the cavity at a plurality of wavelengths, a plurality of absorption peaks of the species to be detected can be examined. Tuning can be effectuated by placing the Bragg grating 110 either in compression or tension. Since optical fiber, typically constructed from quartz, is not very strong in tension, tension tuning only provides a few nanometers shift in wavelength. However, by placing the optical fiber in compression, one can achieve tuning of approximately 40 nm, at a wavelength of 1550 nm. This corresponds to over 150 wave numbers. By way of example, for an absorbing species of carbon dioxide, a 150 wave number sweep allows for detection of two of the three absorption peaks.

Figure 2:
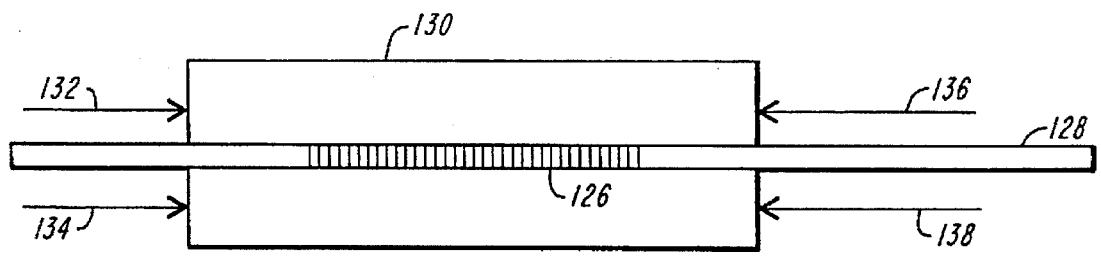
FIG. 2 is a block diagram illustrating a mechanism for compression tuning the Bragg gratings of FIG. 1.

FIG. 2 illustrates a known mechanism for tuning Bragg gratings. As shown, a Bragg grating 126, which is imposed on an optical fiber 128 is threaded axially through a compressible ferrule 130. The ferrule 130 can be compressed at points including, 132, 134, 136 and 138 by way of any conventional selectively adjustable electro-mechanical mechanism. Compression of the ferrule 130 can shift the lasing wavelength in by approximately 40 nm at a wavelength of 1550 nm.

As mentioned above, the optical fiber 108 is lasant-doped with one or more rare earth elements or any element or compound that provides optical gain. Examples of such dopants include: lanthanum, cerium, praseodymium, neodymium, promethium, samarium, europium, gadolinium, terbium, dysprosium, holmium, erbium, thulium and ytterbium. According to one preferred embodiment the fiber is doped with thulium and/or holmium. The concentration with which the fiber is doped is dependent, in part, on the length of the fiber 108. According to one embodiment of the invention, the length of the fiber 108 can range from approximately 3 cm–20 cm and the concentration of the dopant can range from approximately 300 ppm–3000 ppm. By way of example, for a length of approximately 10 cm, a preferred doping concentration of Tm-Ho is approximately 3000 ppm of thulium and 300 ppm of holmium According to a preferred embodiment, the lasing wavelength is chosen based primarily on the species to be detected in the absorption cell 102. For a thulium or thulium-holmium doped fiber, lasing wavelengths in the approximate range of 1.65 microns–2.1 microns can be employed, depending on the ratio of thulium to holmium. This range corresponds to the over tone bands of many molecules. The selection of the pump source 112 is dependent on the rare earth dopant and the lasing wavelength. According to one embodiment, an inexpensive 800 nm laser source 112 can be employed to pump an optical fiber 108 having a Tm-Ho dopant, since thulium absorbs at this wavelength and transfers its energy to holmium. As discussed above, the Bragg grating 110 can be compression tuned to adjust the lasing wavelength. According to one preferred construction, an 800 nm pump is employed with a thulium-holmium dopant, and the Bragg grating 110 is formed to tune the cavity to resonate in the approximate range of 1.8 microns–2.1 microns. In an alternative embodiment, the Bragg grating 110 is formed to resonate the cavity in the approximate range of 1.65 microns–1.8 microns with a thulium dopant.

As shown in FIG. 1, an optical element 106 couples the light from the doped fiber 108 through the absorption cell 102. According to one embodiment, the light coupled from the doped fiber 108 has an initial beam diameter. The initial beam diameter is in the approximate range of 5 microns–20 microns, depending on the size of the optical fiber core. It is desirable to illuminate as much of the sample contained in absorption cell 102 as practical. Accordingly, optical element 106 expands the diameter of the beam 108 to be within the approximate range of 1 mm–5 mm. Such expansion can be accomplished by a gradient index lens, an aspheric lens or any type of lens assembly conventionally employed for such purpose.

There are several methods by which the light from the pump source 112 can be coupled to the resonant cavity and by which a portion of the laser light from the resonant cavity can be coupled to the detector 118. According to one embodiment, the dichroic beam splitter 114 couples light at a first frequency from the pump source 112 to the wavelength-specific reflector 110. The beam splitter 114 also couples light at the lasing frequency from the reflector 110 to the detector 118. Optionally, the filter 120 can filter the light from the laser cavity, prior to coupling it to the detector 118 to ensure that light from the pump source 112 does not couple into the detector 118. Alternatively, a the splitter 114 can be selected to provide sufficient isolation between the pump source 112 and the detector 118.

Figure 3:
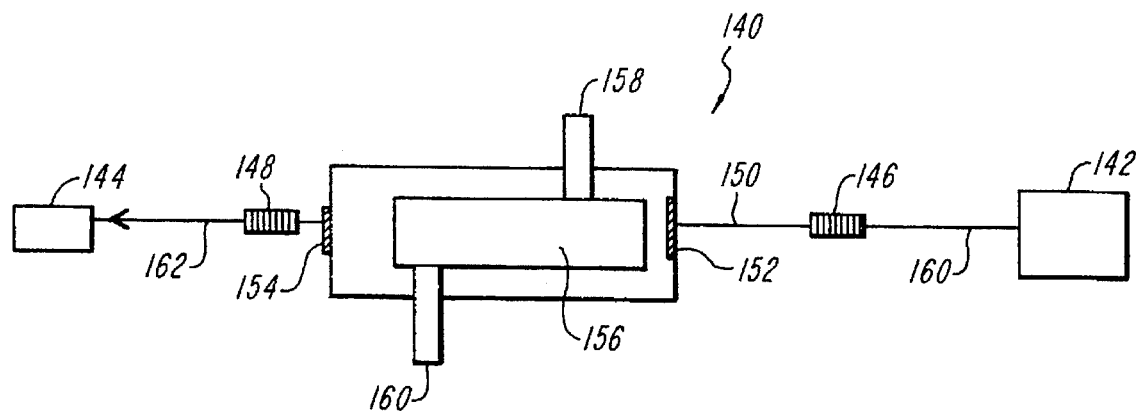
FIG. 3 is a schematic block diagram illustrating an alternate embodiment of the invention wherein an additional Bragg grating is employed in place of the "y" coupler of FIG. 1.

FIG. 3 shows an alternative embodiment of the invention, wherein the dichroic beam splitter is replaced by a second wavelength-specific reflector. As shown in FIG. 3, a spectroscope 140, according to an alternative embodiment of the invention includes a pump source 142, detector 144, and a resonant cavity formed from two wavelength-specific reflectors 146 and 148, a rare earth doped fiber 150 and a pair of optical assemblies 152 and 154. As in the case of the spectroscope of FIG. 1, the resonant cavity of spectroscope 140 can accommodate an absorption chamber 156 having an inlet 158 and an outlet 160. The pump source 142 couples to reflector 146 by way of an undoped fiber 160. Similarly, reflector 148 couples to detector 144 by way of an undoped fiber 162.

As shown in FIG. 3, the wavelength-specific reflectors 146 and 148 are located at distal axial ends of the resonant cavity. Preferably, the reflector 146 is a compressible Bragg grating of the type depicted in FIG. 1, and is formed to reflect light at the selected lasing wavelength. However, unlike the grating of FIG. 1, the grating 146 does not couple light to the detector. The Bragg grating 148 is formed to have a line width at least large as the wavelength range for which the Bragg grating 146 is capable of sweeping the resonant cavity preferably, the Bragg grating 148 is partially transmissive and couples a portion of the laser light from the resonant cavity to the detector 144 along optical fiber 162. By the addition of the second Bragg grating 148, the need for the dichroic beam splitter 114 of FIG. 1 is eliminated. Optical elements 152 and 154, of the type conventionally employed for such purposes, couples light at the lasing wavelength between the reflector 148 and the doped fiber 150. The fiber 150 is doped in the same fashion as fiber 108 of FIG. 1, and the pump source 142 is chosen in a similar fashion to the source 112.

Figure 4:
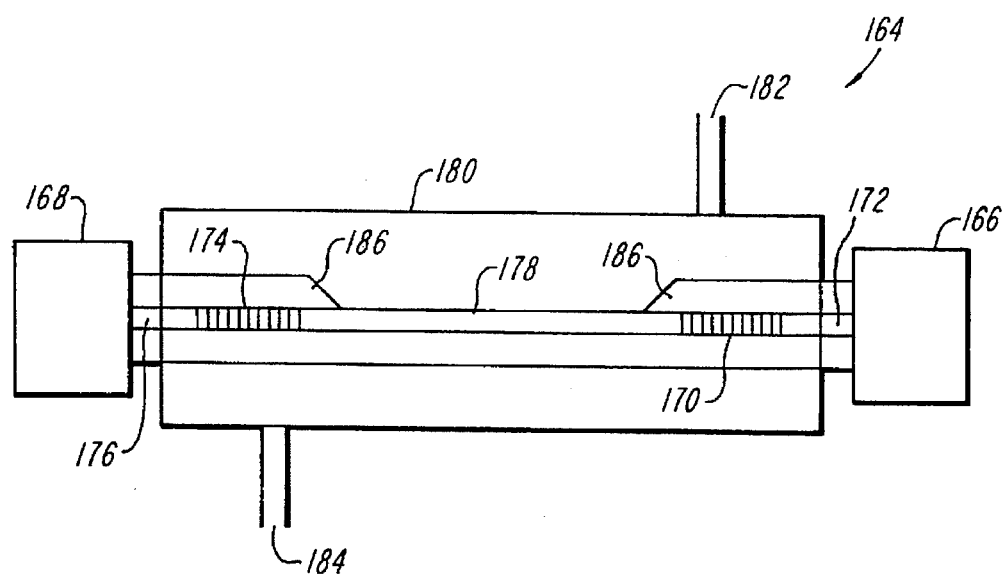
FIG. 4 is a schematic block diagram illustrating an alternate embodiment of the invention wherein evanescent waves are employed to detect an absorber compound.

FIG. 4 is a schematic block diagram for another alternate construction of a spectroscope 164 according to the invention. As in the cases of the embodiments of FIGS. 1 and 3, the spectroscope 164 includes a pump source 166 and a light intensity detector 168. The pump source 166 couples to a wavelength-specific reflector 170 by way of an undoped optical fiber 172. The intensity detector 168 couples to a wavelength-selective reflector 174 by way of an undoped optical fiber 176. The two wavelength-selective reflectors 170 and 174 couple together by way of a rare earth doped fiber 178 to form a resonant cavity. An absorption chamber 180, having an inlet 182 and an outlet 184, surrounds the resonant cavity.

According to a preferred embodiment, the reflector 170 is a compression tunable Bragg grating which is formed to reflect light at the lasing wavelength of the resonant cavity. The reflector 174 is a Bragg grating which is formed to reflect light around the lasing wavelength. It is further formed to have a line width at least as large as the wavelength range through which the grating 170 can be tuned. The reflector 174 is partially transmissive for coupling a small portion of the laser light from the resonant cavity to the intensity detector 168.

As in the case of the embodiments of FIGS. 1 and 3, the pump source 166 couples laser light at a first frequency to the laser cavity by way of the Bragg grating 170. However, unlike the previously discussed embodiments, the laser cavity is formed completely within an optical fiber. The reflectors 170 and 174 reflect light back and forth along the doped fiber amplifier 178 until the cavity resonates at the lasing wavelength. By forming the laser cavity completely within an optical fiber, all of the bulk optical elements can be eliminated. By way of example, there is no need for the expansion lens 106 or the reflector 104 of FIG. 1, nor is there any need for the optical elements 152 and 154 of FIG. 3. Additionally, since the light is completely contained in the optical fiber, the type of alignment traditionally associated with bulk optics is eliminated.

According to the embodiment of FIG. 4, the cladding 186 is removed from at least a portion of the doped fiber core 178 to expose the doped core 178 to the sample to be measured. According to the depicted embodiment, the sample can be contained in the chamber 180. However, according to other embodiments, the spectroscope 164 can be hand held to measure species contained in a room. Evanescent light waves travel on the outside of the doped fiber core 178. If the evanescent waves are exposed to a species which absorbs at the lasing wavelength, the intensity of the those light waves diminishes. In accord with Maxwell's equations, any change in the intensity of the evanescent wave results in a corresponding change in the intensity of the light traveling within the core of the fiber 178. Since the reflector 174 couples a portion of the light from the core 178 to the detector 168, the changes in the light waves propagating on the core can be detected. Such changes can be correlated to the presence of a species in the sample. The changes in intensity can be further correlated, by way of conventional processing methods, to determine the concentration of the species in the sample.

As those skilled in the art will appreciate, components, such as those employed in the above discussed embodiments are readily available from known vendors. By way of example, a mini optical bench of the type employed to align the optical components of FIGS. 1 and 3 can be purchased from Optics For Research, Inc., located in Caldwell, N.J. The lens element 106, 152 and 154, along with the broadband reflector 104 can also be purchased from Optics For Research, Inc. Optical intensity detectors such as those depicted at 118, 144 and 168 can be purchased from EG&G, Inc., located in Quebec, Canada. The pump sources 112, 142 and 166 can be laser diode sources, purchased from EG&G, Inc. or Laser Diode, Inc. of New Jersey. The coupler 114 can be purchased from Gould Fiber Optics, Inc., located in Glen Burnie, Md. The filter 120 is available from CVI, Inc., located in Putnam, Conn.

Other embodiments of the above described device for intra-cavity absorption cell spectroscopy will be obvious to those skilled in the art. By way of example, if it is desirable to detect a plurality of species having different absorption spectrums, a plurality of the above described spectroscopes, each constructed to lase at a different wavelength, can be incorporated into a single measuring device. Thus, additions, subtractions, deletions and other modifications of the preferred described embodiments are within the scope of the claims.

Having described the invention, what is claimed as new and secured by Letters Patent is:

1. A spectroscopic analyzing apparatus comprising:
    a source of excitation energy at a first wavelength;
    a first optic fiber, at least a first portion thereof being lasant-doped, said first optic fiber being optically coupled to said excitation source and at least first portion being capable of lasing at a second wavelength in response to the excitation energy;
    a resonant cavity surrounding said first portion of said optic fiber and having at least a first wavelength-specific reflector such that laser light at said second wavelength is amplified;
    absorption means for exposing a sample to light contained within said resonant cavity; and
    detector means optically coupled to said resonant cavity for detecting variations in the intensity of light produced by absorption of said second wavelength in said resonant cavity by at least a portion of the sample.

2. A spectroscopic analyzing apparatus according to claim 1 wherein said first wavelength-specific reflector comprises a Bragg grating imposed on said first optic fiber to form a periodic variation in refractive index of said first optic fiber.

3. A spectroscopic analyzing apparatus according to claim 2 further comprising compression means coupled to said Bragg grating for selectively compressing said Bragg grating to adjust said second wavelength.

4. A spectroscopic analyzing apparatus according to claim 1 wherein said first wavelength-specific reflector includes means for coupling light at said second wavelength to said detector means.

5. A spectroscopic analyzing apparatus according to claim 2 wherein said Bragg grating includes means for coupling light at said first wavelength into said resonant cavity and means for reflecting light at said second wavelength in said resonant cavity.

6. A spectroscopic analyzing apparatus according to claim 5 wherein said Bragg grating includes means for coupling a portion of said light at said second wavelength to said detector means.

7. A spectroscopic analyzing apparatus according to claim 1 wherein said first portion of said first optic fiber is doped with a concentration in the approximate range of 100 ppm–5000 ppm.

8. A spectroscopic analyzing apparatus according to claim 1 wherein said first portion of said first optic fiber is doped with at least one of holmium and thulium.

9. A spectroscopic analyzing apparatus according to claim 1 wherein said first portion of said first optic fiber is doped with at least one of lanthanum, cerium, praseodymium, neodymium, promethium, samarium, europium, gadolinium, terbium, dysprosium, holmium, erbium, thulium and ytterbium.

10. A spectroscopic analyzing apparatus according to claim 1 wherein said first portion of said first optic fiber has a length in the approximate range of 3 cm–20 cm.

11. A spectroscopic analyzing apparatus according to claim 1 wherein said second wavelength is in the approximate range of 1.8 microns–2.1 microns.

12. A spectroscopic analyzing apparatus according to claim 1 wherein said second wavelength is in the approximate range of 1.65 microns–1.8 microns.

13. A spectroscopic analyzing apparatus according to claim 1 wherein said excitation source is a laser diode.

14. A spectroscopic analyzing apparatus according to claim 1 wherein said first wavelength is approximately 800 nm.

15. A spectroscopic analyzing apparatus according to claim 1 wherein said laser light has an initial beam diameter and said resonant cavity includes expansion means for expanding said laser light to have a subsequent beam diameter prior to said absorption means exposing said sample to said laser light.

16. A spectroscopic analyzing apparatus according to claim 15 wherein said expansion means comprises gradient index lens.

17. A spectroscopic analyzing apparatus according to claim 15 wherein said expansion means comprises an aspheric lens.

18. A spectroscopic analyzing apparatus according to claim 15 wherein said initial beam diameter is in the approximate range of 5 microns–20 microns and said subsequent beam diameter is in the approximate range of 1 mm–5 mm.

19. A spectroscopic analyzing apparatus according to claim 1 further comprising a dichroic beam splitter including means for coupling light from said excitation source at said first frequency into said resonant cavity and means for coupling light at said second frequency from said resonant cavity to said detector means.

20. A spectroscopic analyzing apparatus according to claim 1 wherein said resonant cavity has first and second axial ends, said first wavelength-specific reflector is located at said first axial end, and said resonant cavity includes a second wavelength-specific reflector, located at said second axial end and including means for reflecting light within a predetermined line width of said second wavelength.

21. A spectroscopic analyzing apparatus according to claim 20 wherein said second wavelength-specific reflector includes means for coupling light at said second wavelength to said detector means.

22. A spectroscopic analyzing apparatus according to claim 20 wherein said second wavelength-specific reflector comprises a second optic fiber optically coupled to said second axial end of said resonant cavity and having imposed thereon a Bragg grating to form a periodic variation in refractive index of said second optic fiber.

23. A spectroscopic analyzing apparatus according to claim 22 wherein said Bragg grating includes means for coupling a portion of said light at said second wavelength to said detector means.

24. A spectroscopic analyzing apparatus according to claim 20 wherein said first wavelength-specific reflector comprises a first Bragg grating imposed on said first optic fiber to form a periodic variation in refractive index of said first optic fiber.

25. A spectroscopic analyzing apparatus according to claim 24 wherein said second wavelength-specific reflector comprises a second optic fiber optically coupled to said second axial end of said resonant cavity and having imposed thereon a second Bragg grating to form a periodic variation in refractive index of said second optic fiber.

26. A spectroscopic analyzing apparatus according to claim 25 wherein said second Bragg grating includes means for coupling a portion of said light at said second wavelength to said detector means.

27. A spectroscopic analyzing apparatus according to claim 20 wherein said first wavelength-specific reflector comprises a first Bragg grating imposed on said first optic fiber to form a first periodic variation in refractive index of said first optic fiber proximate to said first axial end of said resonant cavity, and said second wavelength-specific reflector comprises a second Bragg grating imposed on said first optic fiber to form a second periodic variation in refractive index of said first optic fiber proximate to said second axial end of said resonant cavity.

28. A spectroscopic analyzing apparatus according to claim 27 wherein said first Bragg grating includes means for coupling light at said first wavelength into said resonant cavity and means for reflecting light at said second wavelength to said second Bragg grating, and wherein said second Bragg grating includes means for reflecting light at said second wavelength to said first Bragg grating.

29. A spectroscopic analyzing apparatus according to claim 21 wherein said second Bragg grating further comprises means for coupling light at said second wavelength to said detector means.

30. A spectroscopic analyzing apparatus according to claim 27 wherein said laser light amplified in said cavity couples along said first optic fiber between said first Bragg grating and said second Bragg grating, said laser light has an evanescent component and said resonant cavity includes means for exposing said evanescent component to said sample.

31. A spectroscopic analyzing apparatus according to claim 30 wherein said first optical cable has a core portion over which said laser light travels and at least a section of said core portion between said first Bragg grating and said second Bragg is exposed to said sample.

32. A spectroscopic analyzing method comprising the steps of:

doping at least a first portion of a first optic fiber with a lasant;

providing an excitation energy at a first wavelength to said first optic fiber;

forming a resonant cavity around said first portion of said first optic fiber, at least in part by forming a first wavelength-specific reflector on said first optic fiber, such that laser light at a second wavelength is amplified;

exposing a sample to light contained within the cavity; and detecting variations in the intensity of light produced by absorption of the second wavelength in the cavity by at least a portion of the sample.

33. A spectroscopic analyzing method according to claim 32 wherein said step of forming a first wavelength-specific reflector comprises imposing a Bragg grating on said first optic fiber to form a periodic variation in refractive index of said first optic fiber.

34. A spectroscopic analyzing method according to claim 33 further comprising the step of selectively compressing said Bragg grating to adjust said second wavelength.

35. A spectroscopic analyzing method according to claim 32 wherein said step of doping comprises doping at least said first portion of said first optic fiber with at least one of holmium and thulium.

36. A spectroscopic analyzing method according to claim 32 wherein said step of forming said resonant cavity further comprises:

forming said resonant cavity with first and second axial ends;

forming said first wavelength-specific reflector at said first axial end; and forming a second wavelength-specific reflector at said second axial end, such that said second wavelength-specific reflector reflects light within a predetermined line width of said second wavelength.

37. A spectroscopic analyzing method according to claim 36 further comprising the step of coupling light at said second wavelength from said cavity to an intensity detector.

38. A spectroscopic analyzing method according to claim 36 wherein said step of forming said second wavelength-specific reflector comprises coupling a second optical fiber to said second axial end of said resonant cavity and imposing thereon a Bragg grating to form a periodic variation in refractive index of said second optic fiber.

39. A spectroscopic analyzing method according to claim 36 wherein said step of forming said first wavelength-specific reflector comprises imposing a Bragg grating on said first optic fiber to form a periodic variation in refractive index of said first optic fiber, and said step of forming said second wavelength-specific reflector comprises coupling a second optical fiber to said second axial end of said resonant cavity and imposing thereon a second Bragg grating to form a periodic variation in refractive index of said second optic fiber.

40. A spectroscopic analyzing method according to claim 39 comprising the further step of coupling a portion of said light at said second wavelength to said detector means.

41. A spectroscopic analyzing method according to claim 36 wherein said step of forming said first wavelength-specific reflector comprises imposing a Bragg grating on said first optic fiber to form a periodic variation in refractive index of said first optic fiber, and said step of forming said second wavelength-specific reflector comprises imposing a second Bragg grating on said first optic fiber to form a second periodic variation in refractive index of said first optic fiber.

42. A spectroscopic analyzing method according to claim 41 further comprising the steps of coupling light at said first wavelength into said resonant cavity and reflecting light at said second wavelength between said first Bragg grating and said second Bragg grating along said first portion of said first optical fiber.

43. A spectroscopic analyzing method according to claim 42 further comprising the step of exposing an evanescent component of said light reflecting between said first and second Bragg gratings to said sample.

* * * * *